United States Patent [19]
Redmond, Jr. et al.

[11] Patent Number: 5,217,619
[45] Date of Patent: Jun. 8, 1993

[54] LIQUID-SOLID EXTRACTION APPARATUS AND METHOD OF USING SAME

[75] Inventors: Melvin W. Redmond, Jr., Claremont; Thomas J. Good, Sierra Madre, both of Calif.

[73] Assignee: J. T. Baker Inc., Phillipsburg, N.J.

[21] Appl. No.: 846,895

[22] Filed: Mar. 6, 1992

[51] Int. Cl.$^5$ ............................................. B01D 61/14
[52] U.S. Cl. ............................... 210/650; 210/321.75; 210/321.84; 210/406; 210/416.1
[58] Field of Search ........ 210/634, 644, 645, 649–652, 210/195.2, 257.2, 321.72, 321.75, 321.84, 406, 416.1

[56] References Cited
U.S. PATENT DOCUMENTS 4,810,471 3/1989 Wachob et al. ..................... 422/103

FOREIGN PATENT DOCUMENTS 416326A 3/1991 European Pat. Off. .

Primary Examiner—Frank Sever
Attorney, Agent, or Firm—Parmelee, Bollinger & Bramblett

[57] ABSTRACT

System, apparatus and method for efficiently and effectively isolating analytes from a liquid sample by solid phase extraction comprises a workstation platform with a plurality of suction providing stations for receiving either or both a detachably mounted collection chamber housing a removable collection vessel and membrane holder with removable, screen supported disc membrane, the holder having an inlet opening for receiving a liquid and a passageway through the screen supported disc membrane to an exit port for flow and collection, at the appropriate time, of analytes, extraction solvent, or liquid sample. The membrane holder is adapted to be releasably mounted into either the suction stations or the collection chamber. The removable collection vessel in the collection chamber enables prompt, timely, safe and effective removal of solvent, analyte or liquid from the system. The workstation platform is preferably rotatable for ease of access to the plurality of suction providing stations.

10 Claims, 5 Drawing Sheets

LIQUID-SOLID EXTRACTION APPARATUS AND METHOD OF USING SAME

FIELD OF THE INVENTION

This invention relates to system comprising: means, apparatus and method for efficiently and effectively isolating analytes from a liquid sample by solid phase extraction using a solid phase extraction disc membrane. The system and apparatus are easily assembled and disassembled for the various stages of the extraction process. The system apparatus provides for an improved seal of the solid phase extraction membrane so that analyte is not lost from the disc membrane around the circumferential edge thereof. The system and apparatus also provide for a plurality of accessible workstation locations providing a plurality of suctions stations for substantially simultaneous processing of a plurality of liquid samples on a plurality of disc membranes. The apparatus also provides for a convenient means to collect extraction solvent and analytes for safe and environmentally sound disposal thereof and to collect substantially all extracted analyte without loss thereof.

BACKGROUND OF THE INVENTION

Solid phase extraction of analytes from a liquid sample is an increasingly employed method for isolating analyte impurities for analysis thereof. For example, U.S. Environmental Protection Agency Method 525.1 (Rev. 2.2), 1988, sets forth a method for the determination of organic compounds in drinking water by liquid-solid phase extraction and describes apparatus typically used for such methodology. The apparatus described therein is typical of the apparatus used in the art not only for the isolation of analytes from drinking water but for isolating analytes from other liquid samples using solid phase disc membranes.

Such prior art apparatus typically includes a vacuum-/exhaust line connected to a collection flask. The collection flask will have mounted in its top opening, by way of a silicone rubber stopper, a sample holder. Such a sample holder generally comprises a glass frit support on which a solid phase disc membrane is placed and a glass sample holder is then clamped over the disc membrane by means of a metal clamp. Such apparatus is beset by many disadvantages and drawbacks.

The clamp is a generally inadequate means to provide a satisfactory seal around the disc membrane being held between the glass sample holder and glass frit support member and results in loss of analyte around the edges of the disc membrane and contamination of the work area. In the prior art apparatus the extraction solvent and analyte cannot be collected in a separate easily removable, collection vessel. In order to run multiple liquid samples, multiple apparatus set-ups of the type described must be built. The methodology resulting from the use of such a prior art apparatus is neither satisfactory, effective nor efficient.

There is therefore a need for an improved system, apparatus and method for solid phase extraction of analytes from liquid samples that essentially eliminates the aforementioned drawbacks and disadvantages and provides efficient and effective means for conducting such a solid phase extraction process and to enable the operator thereof to efficiently run a plurality of sample extraction process substantially simultaneously.

DRAWINGS

The object of the present invention will become apparent upon the reading of the following description and referring to the accompanying drawings in which similar reference characters represent corresponding parts in each of the several views.

SUMMARY OF THE INVENTION

This invention comprises a system, apparatus and method for conducting liquid-solid phase extraction of analytes from a liquid sample by an effective and efficient means.

Figure 1:
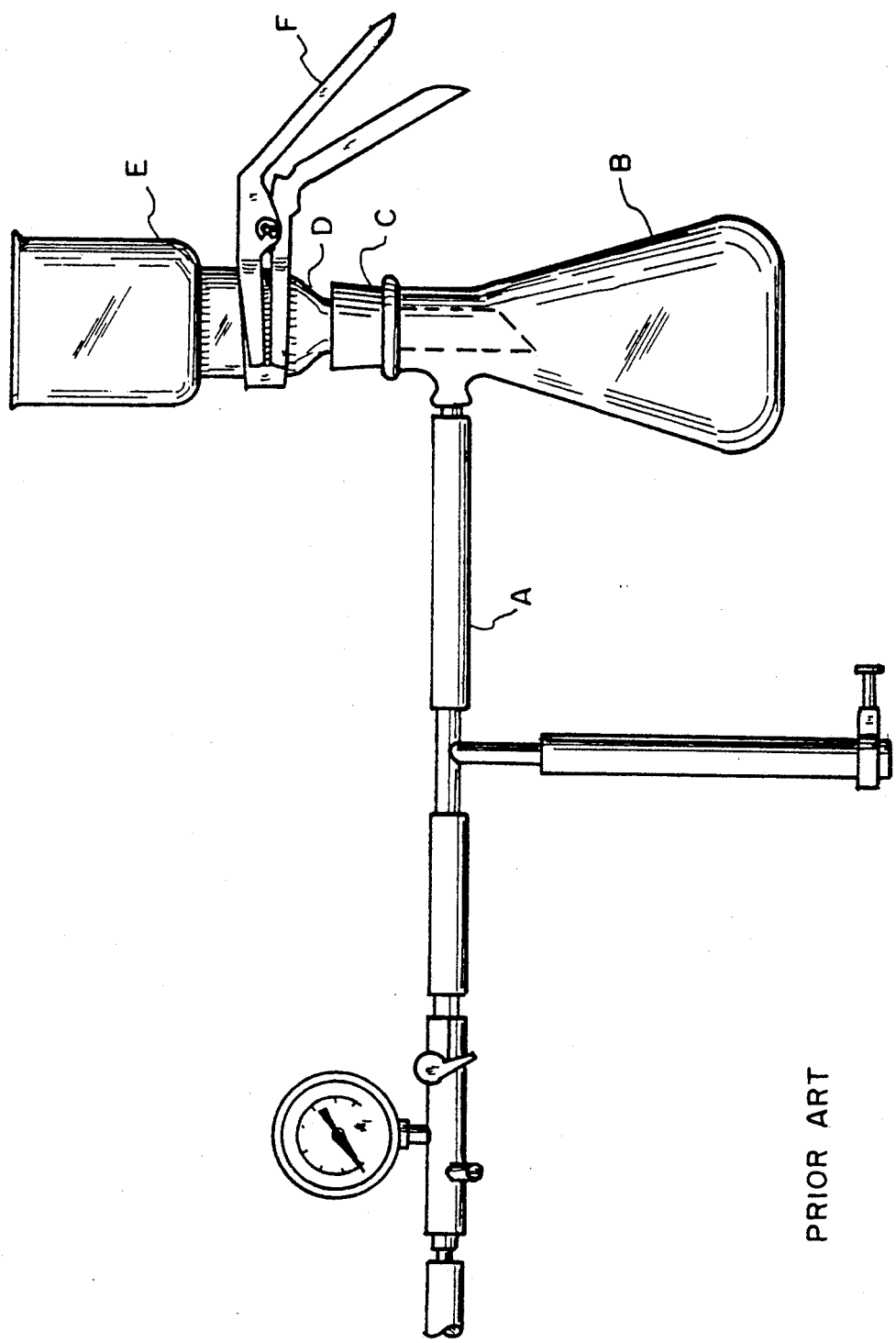
FIG. 1 is a side elevational view of a prior art apparatus set-up.

In FIG. 1 a typical prior art system and apparatus is disclosed. Such a system comprises a vacuum exhaust line A connected to a collection flask B. Mounted in the top entrance to the collection flask E by way of a silicon rubber stopper C is a glass frit membrane support member D on which is laid a disc membrane (not shown) which is held in place by a sample holder overlaying the periphery of the disc membrane and secured to membrane support member D by metal clamp F. The disadvantages and drawbacks of such a system and apparatus have been discussed in the BACKGROUND section of this specification.

The system, apparatus and method of the present invention, is illustrated in FIGS. 2 through 9 to which the reader is now referred.

Figure 2:
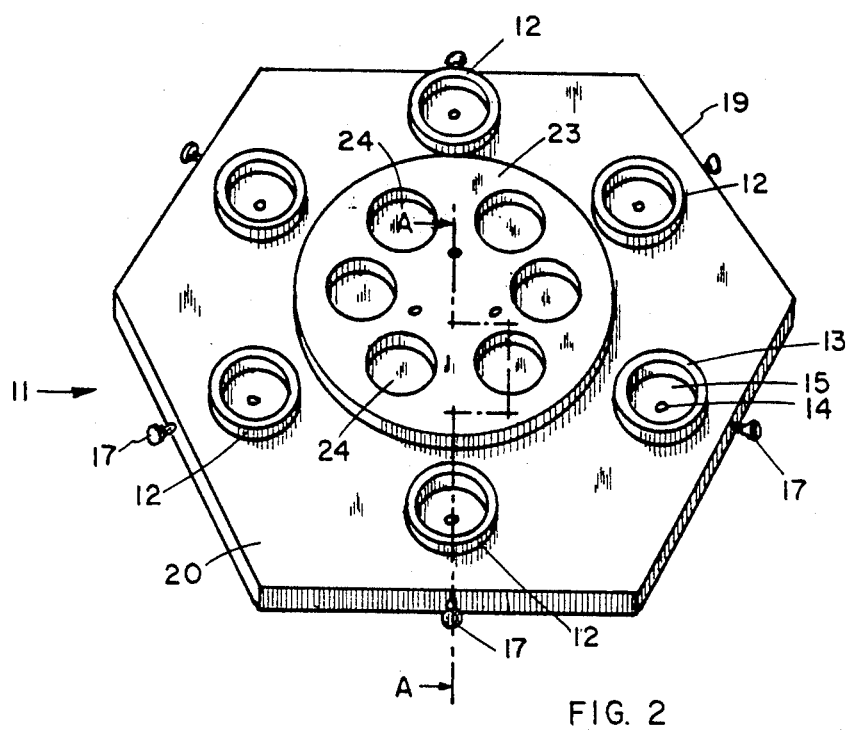
FIG. 2 is a top perspective view of suction providing means of the invention.
Figure 3:
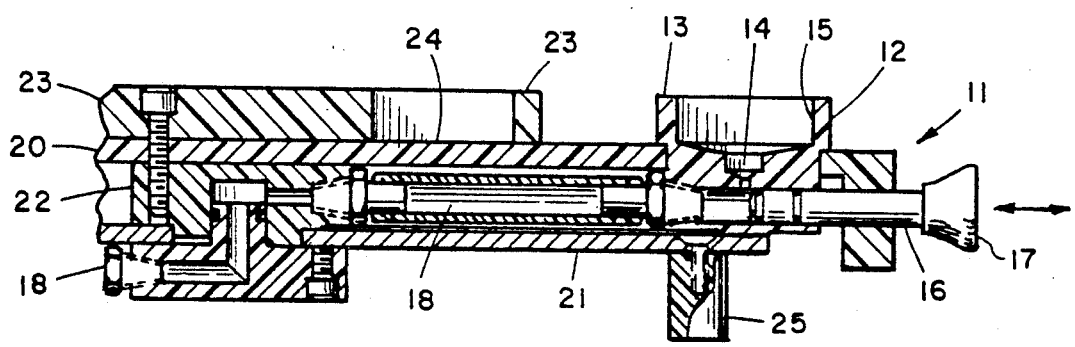
FIG. 3 is a cross-sectional view of the suction providing means taken along line A—A of FIG. 2.

The system and apparatus of the invention has a suction providing means 11 for making suction available at a suction port 14 in a suction station 12, as shown in FIGS. 2 and 3. Station 12 is generally provided by suction station well 15 formed by suction station wall 13. The system preferably provides a plurality of such suction stations 12. A preferred means of providing such plurality of suction stations 12 is to place such stations on a workstation platform 20, generally circumferentially near the outer periphery of the platform. Although the workstation platform 20 itself may rest on a suitable working surface, such as a laboratory bench or table, the platform 20 is preferably mounted by means of hub connecting means 22 to a base support means 21, preferably a metal plate (such as an aluminum plate) having support means 25, generally in the form of downwardly extending legs. Connecting means 22 is adapted to permit platform 20 to rotate on base support 21 to enable an operator of the system to rotate platform 20 so as to move the respective spaced suction stations 12 in front of the operator for ease of use and access thereto.

A suction pathway 18 from a suction source (not shown) leads to suction port 14 of each suction station 12. An adjustable valve 17 for opening and closing pathway 18 to port 14 is provided and may be positioned in the pathway in an open or closed position by means of movable control know 17. FIG. 2 shows the valve in the pathway in an open position.

Platform 20 may be provided with a generally central turret 23 on its upper side, the turret being provided with one or more, preferably a plurality of, storage wells 24 for holding and receiving collection chamber 50 when not in use.

Figure 7:
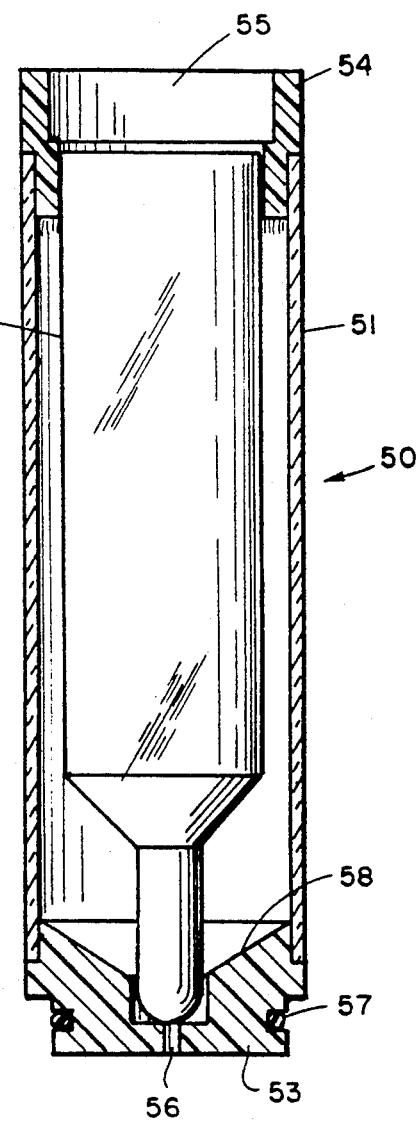
FIG. 7 is a cross-section view of a collection chamber of the apparatus of the invention.

Collection chamber 50, as shown in FIG. 7, may comprise a collection housing 51, preferably a generally cylindrical hollow, transparent (such as glass) housing, and is adapted to receive therein a removable collection vessel 52. At a first end the collection housing 51 is provided with a first mounting means 53 forming a first releasable coupling for insertion into suction station well 15 or storage well 24 and to sealing engage with inner walls of said wells. Preferably, the first mounting and coupling means is provided with an external sealing means 57, such as an O-ring for sealing engaging the inner walls of wells 15 or 24. At the other end of the collection housing 51 there is provided a second mounting means 54 forming a second releasable coupling for receiving and releasably engaging and sealing with membrane housing means 30. Said second mounting means is provided with a central throat opening 55 in which membrane housing means 30 is mounted and releasably received. Collection vessel 52 may comprise for example a suitable sized test-tube or similar container for receiving and holding liquid or analytes.

Figure 4:
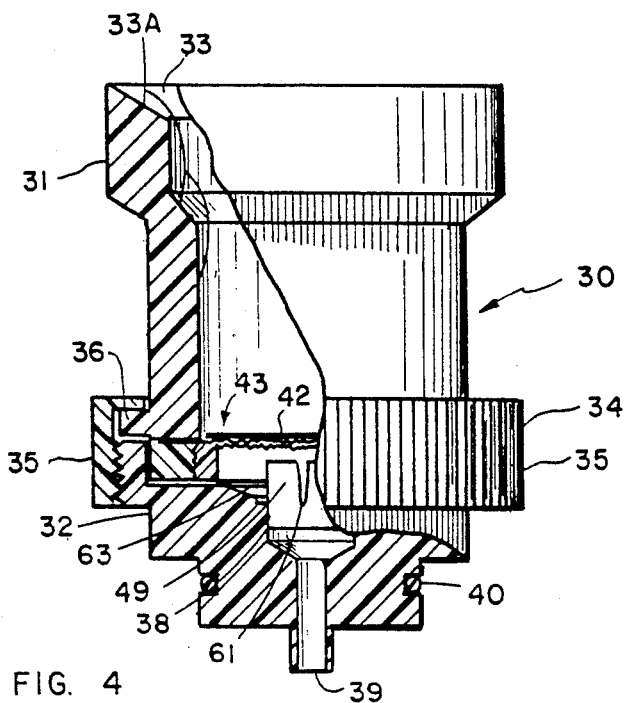
FIG. 4 is an elevational view, partially in section of the membrane holder of the invention.
Figure 5:
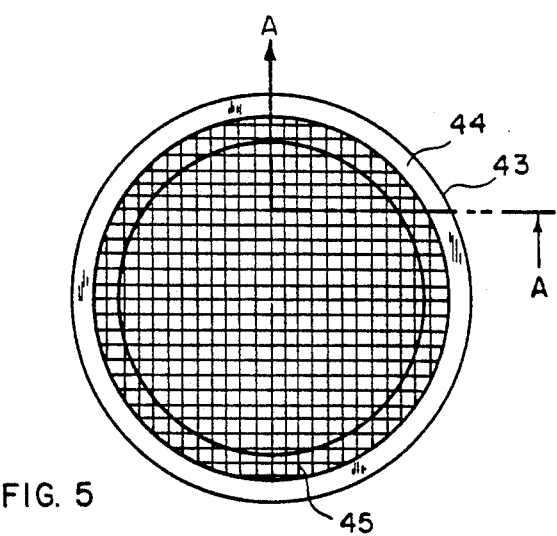
FIG. 5 is a top plan view of the support screen member of FIG. 4.
Figure 6:
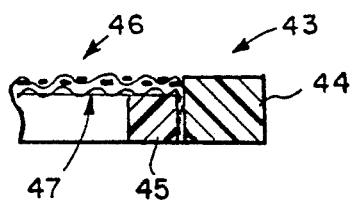
FIG. 6 is a cross-section view of the support screen member of FIG. 5 taken along line A—A.

Membrane housing 30, as shown in FIG. 4, comprises an upper receptacle member 31 detachably securable to a lower membrane holder 32. Upper and lower are to be understood in relation to the suction source when the system is in use, upper being further from the suction source than lower. The upper receptacle is provided at its top end thereof with a funnel like entrance opening 33 for receiving liquid, such as a sample liquid or organic extractant. If desired, the opening 33 provides a guide surface 33A for receiving a sample container 60 containing the liquid having analytes to be extracted. The other, lower end of the upper receptacle 31 is provided with perimeter sealing means 34 for sealing engaging a solid state disc membrane 42 between upper receptacle 31 and membrane holder 32 to prevent liquid flow around rather than through disc membrane 42. Perimeter sealing means 34 may comprise, for example, an outwardly extending annular flange 36 which retains a fastening means 35, such as a downwardly extending inwardly threaded collar, for threading onto a complementary externally threaded upper outer surface 48 on membrane holder 32. Threading collar 35 onto threaded surface 48 brings downwardly extending lip surface 37 into sealing engagement with the outer periphery of disc membrane 42 and screen support means 43 (FIG. 5) on which disc membrane 42 is placed in overlaying relationship. Screen support means 43 may comprise concentric outer and inner rings, 44 and 45, respectively. An upper, small mesh (0.15 mm screen opening), fine gauge (0.1 mm diameter) wire screen 46 and a lower, larger mesh (1.0 mm screen opening), heavier gauge (0.5 mm diameter) wire screen 47 are stretched over hollow inner ring 45 and the inner ring 45 placed into sealing arrangement inside outer ring 44, such that the outer wall of inner ring 45 is in sliding engagement with the inner wall of outer ring 44, as shown in detail in FIG. 6. The screen is preferably polytetrafluoroethylene screening material. Screen support means 43 and disc membrane 42 supported thereby may be additionally supported by membrane support means 38 provided about the central longitudinal axis of membrane holder 32. Membrane support means 38 may comprise upstanding finger members 49 on which screen support means 43 may rest or be drawn against during operation of the suction line, as will be described later. Membrane support means 38 is constructed so as not to impede flow of liquid through the system and if fingers members 49 are provided, liquid flow channels 61 are provided between the finger members.

Membrane holder 32 is provided with an inwardly, downwardly sloping wall 63 forming a flow path for liquid to flow into an outlet port 39. Membrane holder 32 may also be provided with an external sealing means 40, such as an annular O-ring, for sealingly engaging the inner wall surfaces of throat opening 55 and/or suction station well 15.

Figure 8:
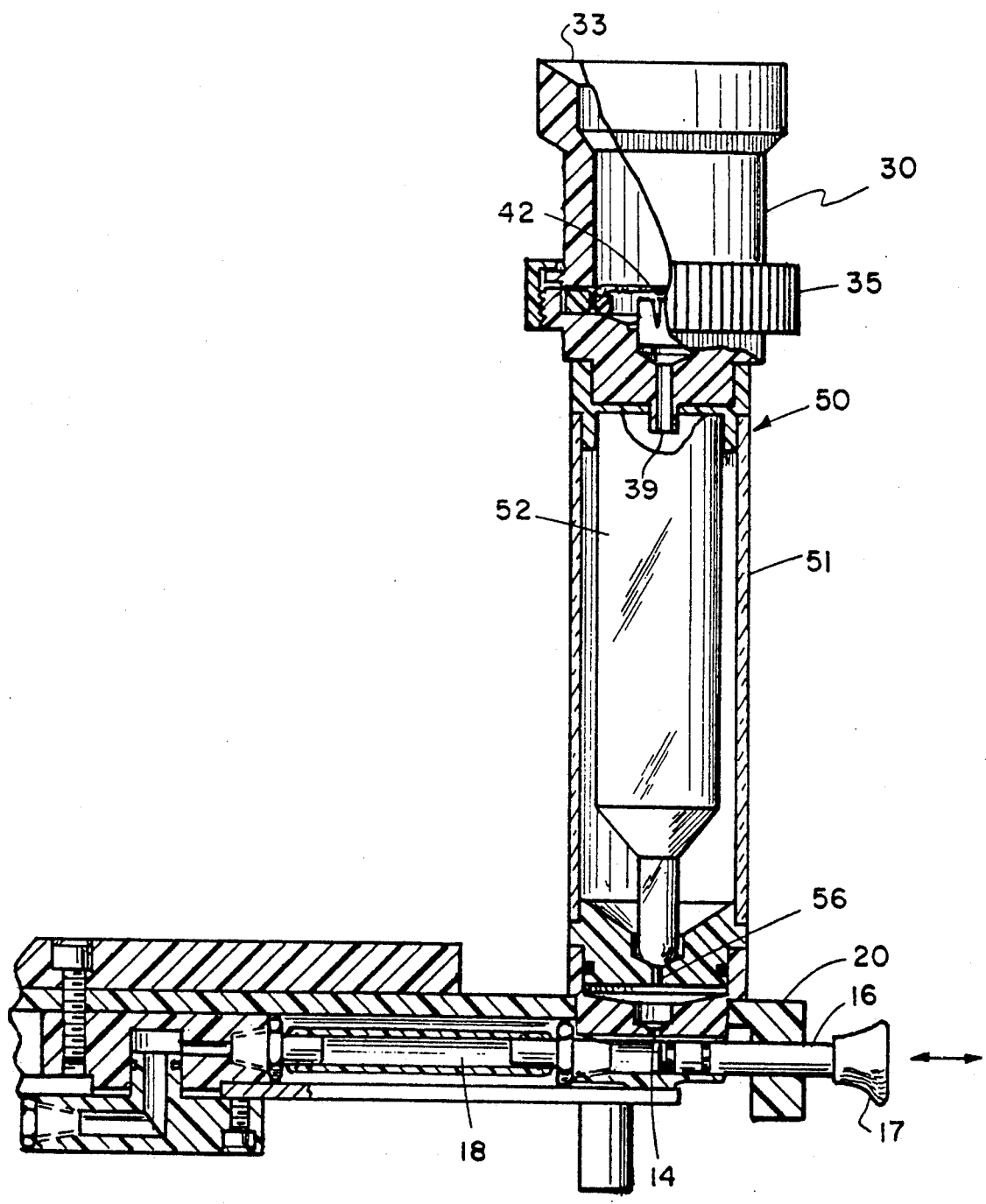
FIG. 8 is an elevation view in partial cross-section showing apparatus assembled for the first and third stage of the process.

The system of this invention permits an operator to conveniently and efficiently conduct a liquid-solid phase extraction process. To carry out the process, a membrane housing 30, in which a disc membrane 42 has been sealing secured as described hereinbefore, is placed in throat opening 54 of collection chamber 50, as shown in FIG. 8, engaging the second mounting and releasable coupling means 54. Collection chamber 50 has been provided with a suitable collection vessel 52 in housing 51 and the first mounting and coupling means thereof 53 is placed into suction station well 15, engaging and sealing with the inner wall thereof. Suction pathway 18 is opened by movement of adjustable valve 16 by pulling on/off knob 17 to the valve open position so that the suction source is connected to suction port 14, and thereby through collection chamber 50 and port 39 to funnel-like entrance 33.

Cleaning solvent is introduced through entrance 33 and cleanses the system, wets and conditions disc membrane 42 and removes any interferants or contaminants in the system. The suction source operates to draw the cleaning solvent through disc membrane 42 and into collection vessel 52. At the conclusion of the cleaning, wetting and conditioning operation, membrane housing 30 is removed from coupling means 54 of collection chamber 50 and collection vessel 52 removed from housing 51. Vessel 52 containing used cleaning solvent may then be handled in a safe and environmentally sound manner to dispose of the used solvent. Collection chamber 50 may then be stored, if desired, in a storage well 24 on turret 23 of workstation platform 20 while stage 2 of the method is conducted.

Figure 9:
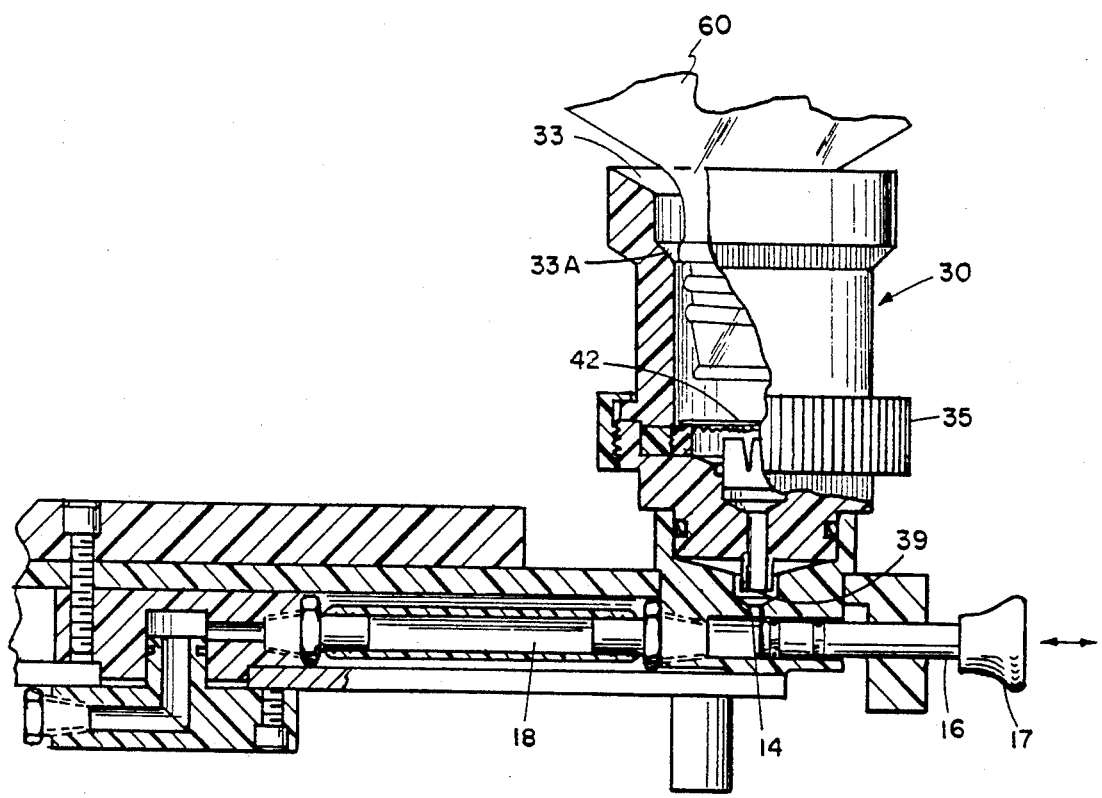
FIG. 9 is a side elevational view in partial cross-section showing the apparatus assembled for the second stage of the process.

In stage 2, membrane housing 30 is now mounted directly into a suction station 12 as shown in FIG. 9. A container 60 with sample liquid to be subjected to the extraction process is placed in entrance 33 and retained therein by guided surface 33A so that the container 60 does not contact or damage disc membrane 42. The sample liquid, for example, one liter of water such as drinking water, is then permitted to flow through disc membrane 42 aided by suction from the suction source through suction station 12. Disc membrane 42 captures the desired analytes by art recognized means known for such disc membranes. As an example of suitable disc membranes useful to extract analytes from water there may be mentioned Empore ™ extraction discs (polytetrafluoroethylene fibrils impregnated with Bakerbond ™ solid phase, such as $C_{18}$ or $C_8$ bonded phase). It will be appreciated that any suitable solid phase disc membrane may be employed in the system, apparatus and method of this invention and that the foregoing is merely illustrative of a type useful for extraction of analytes from water. While the analytes are captured by the disc membrane 42, water from which the analytes have been extracted is allowed to flow through membrane 42, out port 39 into suction station well 15, out suction port 14 and through suction passageway 18 to be disposed of in any suitable manner.

When the sample liquid has traversed through the system and analyte has been retained on membrane 42, the system and apparatus is assembled again into the configuration illustrated in FIG. 8 with a clean collection vessel 52 in collection housing 51 of chamber 50. A small amount of a suitable eluting or extracting solvent, such as methane, is now introduced through entrance 33 of membrane housing 30 in an amount sufficient to elute or extract the analyte from disc membrane 42. Solvent and analyte flow into and are collected in collection vessel 52. Once the elution or extraction step is completed, membrane housing 30 may be removed from throat opening 55 of collection chamber 50 and collection vessel 52 removed and the contents thereof taken for further processing and analysis for the analytes collected therein. Analysis may be by any suitable analytical procedure, such as by IR, UV, LC, GCMS, NMR, immunoassay, or whatever procedure is appropriate for the analysis desired.

After use, the system may be flushed with cleaning solution and the used disc membrane 42 may be removed and replaced with a new membrane and the system is then ready for reuse.

As will be appreciated, the plurality of suction stations 12 provided on workstation platform 20, such as shown in FIG. 2, permit the operator to readily perform a number of extractions substantially simultaneously in a very limited yet conveniently accessible workspace. The system, apparatus and process disclosed also permit improved extraction and retention of analytes and substantially eliminates loss of analyte around the disc membrane 42.

The membrane housing 30, collection chamber coupling means 53 and 54, suction stations 12, workstation platform 20, turret 23 and hub connection 22, are constructed of inert material, such as, for example, polytetrafluoroethylene polymer. Suction pathway 18 may be suitable tubing such as Tygon ® vinyl tubing.

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. A system comprising: means for extraction of analytes from a liquid by liquid-solid phase extraction further comprising:
   (1) A common suction providing means for producing suction available at a plurality of suction ports in a plurality of radially spaced suction stations, each station having a suction port;
   (2) membrane housing means and means for enabling membrane housing means to be releasably mountable at said suction station, said membrane housing comprising solid phase disc membrane sealingly engaged around the outer periphery thereof between (a) an upper receptacle for receiving liquid containing analyte or a container of said liquid and (b) lower membrane holder means retaining said disc membrane, said holder means having a removable screen support means for supporting said disc membrane against a bottom peripheral edge of the upper receptacle, a passageway in said upper receptacle for passage of liquid from a sample, through the disc membrane and out an exit port in said upper receptacle, said exit port being in communication with a suction port of the suction station in which the membrane housing means is releasably mounted.

2. A system according to claim 1 wherein the membrane housing means is releasably mounted at a suction station through a collection chamber, said collection chamber housing a readily removable collection vessel.

3. A system according to claim 1 wherein the screen support means comprises a small mesh, fine gauge wire screen and a larger mesh, heavier gauge wire screen retained over an open inner ring and between a concentric outer ring in sealing engagement with said inner ring.

4. A system according to claim 3 wherein a plurality of suction stations is provided on rotatable workstation platform.

5. A system according to claim 4 wherein said rotatable workstation platform additionally comprises a central raised turret with a plurality of storage wells, each of said wells being adapted to receive and store a collection chamber.

6. A system according to claim 5 wherein the plurality of suction stations are placed circumferentially around the workstation platform near the outer periphery of the platform.

7. A system according to claim 6 wherein the suction providing means comprises suction passageways from the plurality of suction ports to a single suction source, said passageways each having adjustable valves opening and closing said suction passageways.

8. A method comprising: Extracting analytes from a liquid by liquid-solid phase extraction further comprising:
   (1) providing a suction means producing a suction available at a plurality of radially spaced suction ports in a plurality of suction stations, each station having a suction port;
   (2) providing a removable membrane housing and means for releasably mounting removable membrane housing means in a suction station, said membrane housing comprising solid phase disc membrane sealingly engaged around the outer periphery thereof between (a) an upper receptacle for receiving liquid containing analyte or a container and (b) lower membrane holder means retaining said disc membrane, said holder means having a removable screen support means for supporting said disc membrane against a bottom peripheral edge of the upper receptacle, a passageway in said upper receptacle for passage of liquid from a sample, through the disc membrane and out an exit port in said upper receptacle, said exit port being in communication with a suction port of the suction station in which the membrane housing means is releasably mounted;

(3) introducing sample liquid containing analyte in the passageway in said upper receptacle and flowing the sample liquid through the disc membrane, out the exit port, through the suction port into a suction pathway for disposal of the liquid, while retaining analyte on the disc membrane;

(4) after flow of sample liquid is completed, mounting a releasable collection chamber, housing a removable collection vessel, between the membrane housing means and the suction station;

(5) introducing extraction or elution solvent into the passageway in the upper receptacle to elute or extract analyte from the disc membrane and permit analyte to flow through the passageway, out the exit port and into the removable collection vessel; and (6) unmounting the upper receptacle from the collection chamber and removing the collection vessel containing analyte.

9. A solid phase disc membrane support member comprising: a screen support means, said screen support means comprising an outer ring and an inner hollow ring concentric thereto, the outer wall of the inner ring in sliding engagement with the inner wall of the outer ring; a layer of small mesh, fine gauge wire screen overlaying a larger mesh, heavier gauge wire screen; said overlaying screens supported across the hollow inner ring by being held by the sliding engagement of the inner and outer rings and means for sealingly engaging said membrane support member to a suction port of a suction station radially spaced from a suction providing means.

10. The solid phase disc membrane support member of claim 9 wherein a removable solid phase disc membrane overlays said supported screens.

* * * * *